United States Patent [19]

Zagnoli et al.

[11] Patent Number: 4,605,741

[45] Date of Patent: Aug. 12, 1986

[54] PHARMACEUTICALLY ACTIVE SALT DERIVATIVE OF 3-HYDROXY-5-(HYDROXYMETHYL)-2-METHYLISONICOTINALDEHYDE PHOSPHATE

[75] Inventors: Giorgio Zagnoli, Como; Ubaldo Conte; Paolo Colombo, both of Pavia, all of Italy

[73] Assignee: Lisapharma Spa, Erba, Italy

[21] Appl. No.: 797,487

[22] Filed: Nov. 13, 1985

[51] Int. Cl.$^4$ ....................... C07D 401/12; C07F 9/58
[52] U.S. Cl. ....................................................... 546/24
[58] Field of Search ............................. 546/24; 514/76

[56] References Cited

U.S. PATENT DOCUMENTS 2,828,315  3/1958  Wilson ................................. 546/24

Primary Examiner—John M. Ford

Attorney, Agent, or Firm—Stevens, Davis, Miller & Mosher

[57] ABSTRACT

The present invention relates to a novel pharmacologically active salt derivative, constituted by 4-(1-pyrrolidinyl)-1-(2,4,6-trimethoxy-phenyl)-1-butanone 3-hydroxy-5-(hydroxymethyl)-2-methylisonicotinaldehyde-5-phosphate, to the process for the production thereof, and to the related pharmaceutical compositions.

Said salt derivative is produced by reacting 3-hydroxy-5-(hydroxymethyl)-2-methylisonicotinaldehyde-5-phosphoric acid with 4-(1-pyrrolidinyl)-1-(2,4,6-trimethoxyphenyl)-3-butanone in an organic solvent and subsequently crystallizing the reaction product.

Said salt derivative carries out an important pharmacological activity as inhibitor of platelet aggregation with vasodilative action.

1 Claim, No Drawings

PHARMACEUTICALLY ACTIVE SALT DERIVATIVE OF 3-HYDROXY-5-(HYDROXYMETHYL)-2-METHYLISONICOTINALDEHYDE PHOSPHATE

The present invention relates to a novel pharmaceutically active salt derivative, and namely to 4-(1-pyrrolidinyl)-1-(2,4,6-trimethoxyphenyl)-1-butanone 3-hydroxy-5-(hydroxymethyl)-2-methylisonicotinaldehyde-5-phosphate, having the following structural formula:

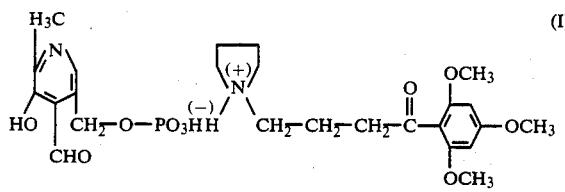

The present invention relates also to the process for the production of the salt derivative (I) and to the related pharmaceutical compositions.

The salt derivative (I) is obtained by means of the salifying of 3-hydroxy-5-(hydroxymethyl)-2-methylisonicotinaldehyde-5-phosphoric acid with 4-(1-pyrrolidinyl)-1-(2,4,6-trimethoxyphenyl)-1-butanone.

The pharmaceutical activity of the two starting products is known. In particular, the pharmacological activity is known of 4-(1-pyrrolidinyl)-1-(2,4,6-trimethoxyphenyl)-1-butanone hydrochloride (Buflomedil) on the cerebral circle for the treatment of disturbances of consciousness, and of states consequent to cerebral traumata, and its peripheral vasodilative properties are known too.

As for 3-hydroxy-5-(hydroxymethyl)-2-methylisonicotinaldehyde-5-phosphoric acid (Piridoxal phosphate), it is known as an enzyme co-factor vitamin.

From the reaction of these two products, the obtaining could be expected of a drug having vasodilating activity and, at the same time, vitaminic activity, useful for the handling of pathological forms in old people.

On the contrary, we have unespectedly found that from such a reaction a drug is obtained with antithrombotic activity, which is to be added to the vasodilative action of Buflomedil, which is not modified.

It is to be noted that no one of the presently used drugs shows a combination of antithrombotic action and of peripheral vasodilative action.

The salt derivative (I) according to the present invention shows hence a platelet aggregation inhibitor and a vasodilator activity in one single molecule and is hence directed to the treatment of clinical patterns characterized by peripheral failure, clinical patterns to be found with particular frequency in old people, with a wider and more complete efficacy than Buflomedil.

The salt derivative (I) according to the invention shows moreover, relatively to Buflomedil, the further advantage of a high solubility in water, which favours its bioavailability and allows it to be administered by the parenteral and the rectal way.

The salt derivative (I) according to the present invention is prepared by means of a process characterized in that 3-hydroxy-5-(hydroxymethyl)-2-methylisonicotinaldehyde-5-phosphoric acid is reacted with 4-(1-pyrrolidinyl)-1-(2,4,6-trimethoxyphenyl)-1-butanone in a reaction medium constituted by an organic solvent in which (I) is soluble, and the reaction product (I) is crystallized from an organic solvent wherein it is insoluble. The characteristics and the advantages of the salt derivative (I) and of the related production process shall be better evidenced by the following disclosure, which relates to a preferred embodiment.

For the preparation of the salt derivative (I), 3-hydroxy-5-(hydroxymethyl)-2-methylisonicotinaldehyde-5-phosphoric acid is previously liberated from its monosodium salt in a column with strongly basic ion exchange resin activated as chloride. The aqueous solution of 3-hydroxy-5-(hydroxymethyl)-2-methylisonicotinaldehyde-5-phosphoric acid so obtained is concentrated to dryness, a yellow oily residue being obtained, which is redispersed three times with small portions of absolute ethanol, to remove water. The residue is finally treated with anhydrous ethyl acetate, a product being obtained which is filtered and dried in a vacuum desiccator.

3-Hydroxy-5-(hydroxymethyl)-2-methylisonicotinaldehyde-5-phosphoric acid so obtained is dispersed in methanol, in which it is not soluble, and solid 4-(1-pyrrolidinyl)-1-(2,4,6-trimethoxyphenyl)-1-butanone is added under stirring. The reaction mass is then heated to a temperature comprised within the range of from 40° C. to the solvent refluxing temperature, and, preferably, to a temperature comprised within the range of from 45° to 55° C., a clear yellow solution being obtained, which even after cooling, does not yield any precipitates. The solution is concentrated up to complete removal of methanol, is then redispersed with ethyl ether, and after shaking the salt derivative (I) is obtained as crystals, which is filtered, washed with ethyl ether and dried in a vacuum desiccator.

The salt derivative (I) obtained is a crystalline powder of yellow colour, very soluble in water and aliphatic alcohols, whilst it is insoluble in ethyl ether. The crystallization of the raw product is carried out from a blend of aliphatic alcohols and ethyl ether, up to the required purity degree. The yield of each crystallization is of about 90%.

The characterization of said product was carried out by: X-ray diffractometry, I.R., U.V., and NMR spectrography and by means of the determination of the melting temperature and of pH.

The crystallographic analysis by X-ray diffractometry demonstrates that the product is a single substance deriving from the formation of a ionic bond between the two reactants.

In the following Table 1 the characteristic peaks (diffraction angles $\theta$ and interplanar distances (d), $\lambda_{Cu} = 1.5418$ Å, and the intensity on relative scale $I_{rel}$ are reported for the salt derivative (I) according to the invention, and, for comparison purposes, for the two reactants (Buflomedil and Pyridoxal phosphate).

|   |   | $2\theta_{Cu}$ | d | $I_{rel.}$ |
|---|---|---|---|---|
| 1. BUFLOMEDIL Base | a | 19.7 | 4.51 | (9.0) |
|  | b | 16.3 | 5.44 | (7.8) |
|  | c | 15.9 | 5.57 | (7.5) |
|  | d | 23.9 | 3.72 | (7.0) |
|  | e | 25.7 | 3.47 | (5.8) |
| 2. SODIUM PYRIDOXAL PHOSPHATE (acid) | a | 4.2 | 21.04 | (1.6) |
|  | b | 17.6 | 5.04 | (1.1) |
| 3. SALT DERIVATIVE (I) | a | 24.2 | 3.68 | (2.9) |
|  | b | 20.5 | 4.33 | (2.0) |
|  | c | 24.7 | 3.60 | (1.8) |

| | $2\theta_{Cu}$ | d | $I_{rel.}$ |
|---|---|---|---|
| d | 15.3 | 5.79 | (1.6) |
| e | 12.4 | 7.14 | (1.5) |

It results from this Table that no characteristic peaks of the reactants are present in the salt derivative (I), and vice-versa; in the salifying of the reactants a new crystalline phase has hence been obtained.

The I.R. absorption spectrum carried out in Nujol shows characteristic absorption peaks at the following wavelengths:

at ... 2720 cm$^{-1}$ absorption band of aldehydic —CH
at ... 1695 cm$^{-1}$ absorption band of ketonic carbonyl
at ... 1665 cm$^{-1}$ band of the aldehydic carbonyl
at ... 1460 and 1375 cm$^{-1}$ bands of the aromatic double bond.

The absorption spectrum of a solution in ethanol shows an absorption peak at 283 ±1 nm.

At the NMR spectrum the following signals are detected:

| | | |
|---|---|---|
| at 2.1 s | 3 H | (CH$_3$) Pyr |
| at 3.7 s | 9 H | (OCH$_3$) B |
| at 3.9 s | 3 H | (1CH$_3$) |
| at 5.95 s | 2 H | (Aromatics) B |
| at 4.16 q | 1 H | (1CH) |
| at 7.22 s | 1 H | (Aromatics) P |
| at 7.95 s | 1 H | (Aromatics) P |
| from 7.16 to 8.23 m | 10 H | (Aromatics) |
| at 10.4 s | 1 H | (aldehydic —CH) P |
| at 10.5 s | 1 H | (1NH) |

The melting temperature, as measured on Kofler block, is well defined at 77°–80° C.

pH, as determined in a 2% aqueous solution, is of 7.0. As for the pharmaceutical compositions, wherein the salt derivative (I) according to the present invention may enter as the active principle, it can be observed that, due to its high solubility in water, with it all the pharmaceutical forms can be prepared, both for oral and rectal administering, and for the injectable and topic way, in combination with the usual excipients and with the conventional pharmaceutical media.

To the purpose of illustrating, without limiting, the process according to the present invention, the following Example is reported.

EXAMPLE 1

In a column about 700 ml of (moist) strongly basic ion exchange resins are activated with a 5% HCl solution, and the resin is washed up to the removal of the excess of hydrochloric acid. After that, through the column a 20% solution of 50 g of monosodium 3-hydroxy-5-(hydroxy-methyl)-2-methyl-isonicotinaldehyde-5-phosphate is passed. The mass inside the column is finally washed with water up to neutral pH. The so-obtained aqueous solution of 3-hydroxy-5-(hydroxymethyl)-2-methyl-isonicotinaldehyde-5-phosphoric acid is concentrated to an oil which is redispersed three times in an amount of absolute ethanol which is nearly threefold relatively to the weight of the residue. After the removal of water, the residue is redispersed in 200 ml of anhydrous ethyl acetate, within which a yellow precipitate is formed under shaking, which is vacuum filtered.

The filtrate is washed with anhydrous ethyl acetate and vacuum dried.

An amount of 42.5 g of 3-hydroxy-5-(hydroxymethyl)-2-methylisonicotinaldehyde-5-phosphoric acid (C$_8$H$_{10}$NO$_6$P, m. w.=247.156) ready for the salifying is obtained (yield 85%). In 380 ml of methanol 40 g of 3-hydroxy-5-(hydroxymethyl)-2-methylisonicotinaldehyde-5-phosphoric acid are dispersed and, always at room temperature and under stirring, 56 g are introduced of 4-(1-pyrrolidinyl)-1-(2,4,6-trimethoxyphenyl)-1-butanone (C$_{17}$H$_{26}$NO$_4$, m.w.=307.4).

The system is heated at 50° C. until a single phase is obtained. One is so sure that the salifying has taken place, on considering the insolubility of 3-hydroxy-5-(hydroxymethyl)-2-methylisonicotinaldehyde-5-phosphoric acid even at high temperature.

The solution obtained is cooled, is concentrated in vacuo until the methanol, solvent wherein the solubility of the salt derivative (I) is such as to prevent the crystallizing, has been completely removed. After that the methanol has been removed, the residue is dispersed in 480 ml of ethyl ether, and is then filtered and dried in a desiccator in vacuo at room temperature.

An amount of 76.8 g of 4-(1-pyrrolidinyl)-1-(2,4,6)-trimethoxyphenyl)-1-butanone 3-hydroxy-5-(hydroxymethyl)-2-methylisonicotinaldehyde-5-phosphate (C$_{25}$H$_{36}$N$_2$O$_{10}$, m.w.=554.576) is obtained, with an active salifying yield of 80%. The salt derivative (I) obtained has a melting point of 77°–80° C.

The subsequent crystallizations from methanol-ethyl ether yield the product with the desired purity level.

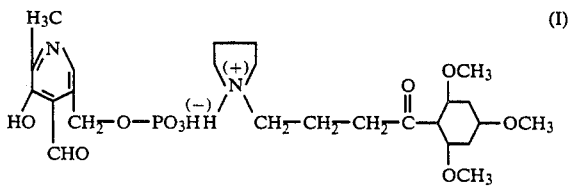

We claim:

1. Pharmacologically active salt derivative constituted by 4-(1-pyrrolidinyl)-1-(2,4,6-trimethoxyphenyl)-1-butanone 3-hydroxy-5-(hydroxymethyl)-2-methylisonicotinaldehyde-phosphate, having the following structural formula: